US010495586B2

(12) United States Patent
Bogumil et al.

(10) Patent No.: US 10,495,586 B2
(45) Date of Patent: Dec. 3, 2019

(54) APPARATUS FOR NONDESTRUCTIVE MATERIAL TESTING OF OBJECTS

(71) Applicant: YXLON INTERNATIONAL GMBH, Hamburg (DE)

(72) Inventors: Frank Bogumil, Bad Segeberg (DE); Reinhard Krüger, Hamburg (DE); Joscha Malin, Hamburg (DE); Jürgen Melchert, Bad Oldesloe (DE); Florian Freiherr Von Oldershausen, Hamburg (DE); Erhard Ottens, Kiebitzreihe (DE); Heiko Schlüter, Kollmar (DE)

(73) Assignee: YXLON INTERNATIONAL GMBH, Hamburg (DE)

( * ) Notice: Subject to any disclaimer, the term of this patent is extended or adjusted under 35 U.S.C. 154(b) by 139 days.

(21) Appl. No.: 15/756,952

(22) PCT Filed: Aug. 29, 2016

(86) PCT No.: PCT/EP2016/001456
§ 371 (c)(1),
(2) Date: Mar. 1, 2018

(87) PCT Pub. No.: WO2017/041877
PCT Pub. Date: Mar. 16, 2017

(65) Prior Publication Data
US 2018/0356353 A1    Dec. 13, 2018

(30) Foreign Application Priority Data

Sep. 7, 2015   (DE) ................ 10 2015 011 435

(51) Int. Cl.
*G01N 23/04*  (2018.01)
*G01N 23/18*  (2018.01)
*G01M 17/02*  (2006.01)

(52) U.S. Cl.
CPC ........ *G01N 23/185* (2013.01); *G01M 17/028* (2013.01); *G01N 2223/627* (2013.01)

(58) Field of Classification Search
None
See application file for complete search history.

(56) References Cited

U.S. PATENT DOCUMENTS

| 4,205,216 | A | * | 5/1980 | Douglas | ................. | B23K 26/02 |
| | | | | | | 198/950 |
| 5,740,221 | A | * | 4/1998 | Norman | ................. | G01N 23/04 |
| | | | | | | 378/57 |

(Continued)

FOREIGN PATENT DOCUMENTS

| DE | 4112470 | 10/1992 |
| DE | 19746594 | 7/1998 |

(Continued)

OTHER PUBLICATIONS

IPRP 03132018, English translation of the International Preliminary Report on Patentability; dated Mar. 13, 2018; 7 pages.

(Continued)

*Primary Examiner* — Hoon K Song
(74) *Attorney, Agent, or Firm* — Lempia Summerfield Katz LLC

(57) ABSTRACT

The invention relates to a device for non-destructively material testing objects, in particular rims and wheels (12), comprising an X-ray inspection cabin (14) which contains an X-ray inspection device (28) for X-raying the objects and comprising conveyor devices (34, 36, 56, 68, 98) for conveying objects through at least one lock (20, 22) into the X-ray inspection cabin (14) and out of the X-ray inspection cabin (14). The aim of the invention is to prevent a leakage of X-rays into the surrounding area through the lock (20, 22) and to reduce the quantity of lead needed for shielding and optionally the space requirement of the device (10). Accord- (Continued)

ing to the invention this is achieved in that the lock (20, 22) comprises a hollow cylinder (60), the circumferential wall (62) of which has a through-opening (64) for the objects and which can be rotated about a horizontal rotation axis in order to position the through-opening (64) on a lock (20, 22) side facing away from the X-ray inspection cabin (14) or the lock (20, 22) side facing the X-ray inspection cabin (14) in an alternating manner.

17 Claims, 5 Drawing Sheets

(56) References Cited

U.S. PATENT DOCUMENTS

| | | | |
|---|---|---|---|
| 7,626,186 | B2 | 12/2009 | Kang et al. |
| 8,391,440 | B2 * | 3/2013 | Hills ................. A61B 6/107 |
| | | | 378/203 |
| 8,513,623 | B2 * | 8/2013 | Newman ................. A61L 2/081 |
| | | | 250/455.11 |
| 2008/0131312 | A1 | 6/2008 | Kung et al. |
| 2008/0131315 | A1 * | 6/2008 | Takase ............... G01N 21/7703 |
| | | | 422/52 |

FOREIGN PATENT DOCUMENTS

| | | |
|---|---|---|
| DE | 102007000305 | 1/2008 |
| EP | 1340512 | 9/2003 |
| EP | 2253947 | 11/2010 |
| WO | 03085416 | 10/2003 |

OTHER PUBLICATIONS

Search Report dated Oct. 26, 2016, International Search Report cited in the corresponding PCT/EP2016/001456; dated Oct. 26, 2016; 6 pages.

* cited by examiner

APPARATUS FOR NONDESTRUCTIVE MATERIAL TESTING OF OBJECTS

RELATED APPLICATION DATA

This application is a U.S. national stage of and claims priority benefit to prior filed international application no. PCT/EP2016/001456, filed Aug. 29, 2016, and which claims priority to German national application no. 10 2015 011 435.2, filed Sep. 7, 2015. The entire contents of these prior filed applications are hereby incorporated by reference herein.

BACKGROUND

1. Field of the Disclosure

The invention relates to an apparatus for nondestructive material testing of objects, in particular rims or wheels of light metal casting, having a x-ray chamber that contains a fluoroscopy device for fluoroscopy of the objects, and having conveyor devices for conveying the objects through at least one lock into the x-ray chamber and out of the x-ray chamber.

Motor vehicle wheels made of light metal casting, before being used, must be subjected to nondestructive material testing, which makes it possible to reject wheels with casting flaws. For that purpose, apparatuses of the type recited at the outset are used, in the x-ray chambers of which various portions of the vehicle rims undergo fluoroscopy in succession using X-radiation.

2. Description of Related Art

Such apparatuses are known from EP 2 253 947 A1 and WO 03/085416 A1, among others. These apparatuses each include a x-ray chamber, in which an X-ray source and an image detector are located, as well as two lock chambers, which are located upstream and downstream of the x-ray chamber in terms of the transporting direction of the wheels. Passages for the wheels are located in the walls between the chambers and are closable by means of bulkheads, in order to prevent X-radiation from escaping from the x-ray chamber. If a wheel is to be conveyed out of the first lock chamber into the x-ray chamber, or from the x-ray chamber into the second lock chamber, the respective associated bulkhead is opened.

Since the service life of X-ray sources decreases when the sources are switched on and off frequently, the X-ray sources are preferably kept on permanently. As a result, however, when a bulkhead is opened X-radiation can pass through the passage into the adjacent lock chamber. To prevent this X-radiation from escaping outside to the surroundings and thereby exposing the equipment operators to an excessive radiation dose, in the apparatus known from EP 2 253 947 A1, a bulkhead is also provided at the inlet to the first lock and at the outlet of the second lock. This bulkhead is closed before the bulkhead between the lock chamber and the x-ray chamber is opened. For detecting the closing and opening status of the bulkheads, however, switches are necessary, whose proper function must always be ensured. On account of the X-radiation penetrating the lock chambers through the passages, not only the walls, ceiling and floor of the x-ray chamber but also the walls, ceiling and floor of the lock chambers must furthermore be provided with a shield made of a material that contains lead, and a large amount of lead is needed for the purpose.

From U.S. Pat. No. 5,749,221 and German Patent DE 197 46 594 C2, an apparatus as defined by the preamble of claim 1 is already known in which the rotary axis of the hollow cylinder is oriented vertically and perpendicular to a rectilinear horizontal transportation path of the objects. On account of the relative motion of the conveyor with respect to the hollow cylinder, however, a radiation-impermeable sealing between the lower end face of the hollow cylinder and the supporting surface of the conveyor is practically impossible to achieve, thus requiring that a lock chamber surrounding the hollow cylinder be entirely lined with lead.

From DE 41 12 470 A1, it is known to feed baggage through a chamber and expose it to a negative pressure in the chamber. The chamber has a lock at the entrance that comprises both a stationary hollow cylinder which has two opposed openings in its circumferential wall and a star-shaped cell wheel which is rotatable about a horizontal rotary axis and the cells of which can be moved alternately in front of one of the two openings as a result of the rotation.

SUMMARY

Based on this, it is the object of the invention to improve an apparatus of the type defined at the outset such that an escape of X-radiation through the lock or locks into the surroundings can be prevented with little effort, the amount of lead needed for the shielding can be reduced, and as applicable the space needed for the apparatus can be reduced.

This object is attained according to the invention by the features in claim 1. The at least one lock includes a hollow cylinder, whose circumferential wall has a through opening for the objects and which is rotatable about a rotary axis oriented transversely to the transporting direction of the conveyor devices, in order to position the through opening alternately on a side of the lock facing away from the x-ray chamber or on a side of the lock facing toward the x-ray chamber. According to the invention, the rotary axis is oriented horizontally, so that it is parallel to the supporting surface of the conveyor device.

Since the circumferential wall of the hollow cylinder has only a single through opening, it can be ensured that the lock is never open to both the x-ray chamber and to the opposite side, so that a direct passage of X-radiation through the lock can be securely prevented. Moreover, by means of a shield of lead-containing material that is located on the circumferential wall and on the opposed face ends of the hollow cylinder, it can be ensured that X-radiation, which reaches the hollow cylinder when the passage between the lock and the x-ray chamber is open, cannot exit again from the hollow cylinder. Since the surface area of the circumferential wall and of the face ends of the hollow cylinder is markedly smaller than the surface area of the walls, ceiling and floor of a lock chamber surrounding the hollow cylinder, it is furthermore possible to reduce the quantity of lead required for the shielding considerably. Moreover, the space required for the apparatus can be reduced because the width of the lock chamber is adapted to the axial length of the hollow cylinder by moving the side walls closer to the face ends of the hollow cylinder.

The apparatus of the invention is preferably used for nondestructive material testing of rotationally symmetrical rims or wheels made of light metal casting, but in principle it can also be used for nondestructive material testing of arbitrary other objects.

In the nondestructive material testing the objects are preferably conveyed through the x-ray chamber; they enter it on one side and emerge from it on the opposite side. In that case, two essentially structurally identical locks or lock chambers are provided, one upstream and one downstream of the x-ray chamber. Alternatively, however, the objects could also enter the x-ray chamber on one side and emerge again on the same side; in that case, a single lock or lock chamber suffices. The first case above, which is preferred, will be described hereinafter.

To make it possible for the objects to be conveyed through the hollow cylinders of the locks, each lock advantageously has a conveyor, which is located entirely in the interior of the hollow cylinder; its opposed ends are expediently spaced apart slightly from the circumferential wall. As a result, the hollow cylinder is rotatable about the conveyor located inside the hollow cylinder, in order to locate the through opening alternately in front of the front and rear ends, in terms of the direction of transportation, of the conveyor.

In addition, the conveyor devices have further conveyors, which are located inside the x-ray chamber as well as on the sides of the locks or lock chambers that are opposite from the x-ray chamber, and advantageously, like the conveyors in the locks, have a support surface for the objects that is horizontal and parallel to the rotary axes of the hollow cylinders. In order to make optimal use of the interior of the hollow cylinders, this supporting surface is advantageously located at a distance below the rotary axis of the hollow cylinders.

In principle, it is possible for each hollow cylinder to be embodied as closed at one of its ends and similarly to the drums of a front-loading washing machine to be supported rotatably at one of the two side walls of the associated lock chamber. In that case, the conveyor located in the hollow cylinder is supported by cantilevered braces, which extend through the open end of the hollow cylinder and expediently are supported on the floor of the lock chamber. Moreover, the closed end of the hollow cylinder is then itself provided with a shield of lead-containing material, while on the opposite open end, the shield of a lead-containing material is advantageously applied to the adjacent side wall of the lock chamber.

Preferably, however, the hollow cylinder has two open ends. In that case, the braces that support the conveyors advantageously extend through both open ends of the hollow cylinder to the floor of the lock chamber. Furthermore, the shields of the lead-containing material are then mounted opposite from both open ends of the hollow cylinder, on the side walls of the lock chamber. For this reason as well, it is advantageous to shift the side walls as close as possible to the ends of the hollow cylinder.

For maintenance purposes, at least one of the two side walls of the lock chamber has a large door or is embodied as a door, preferably a side wall which is opposite one open end of the hollow cylinder so that the hollow cylinder can be pulled, in the direction of its rotary axis, out of the lock chamber.

The shield at the circumferential wall and at the end or ends of the hollow cylinder and on the side wall or walls of the lock chambers expediently comprises a covering of sandwich material, which includes one layer of lead between two layers of steel. Except for the shield, which is provided opposite from the open end or ends of the hollow cylinder, in both cases either a further shield with a lead-containing material on the walls, ceiling and floor can be dispensed with, or this shield can be embodied with a considerably smaller amount of lead as consequence of a greatly reduced exposure to radiation.

Nevertheless it is advantageous to provide further lead-containing material for shielding in the vicinity of the gaps that are located between the rotating hollow cylinder and adjacent stationary surfaces, so that no radiation can escape from the hollow cylinder through these gaps.

For this purpose it is advantageous, opposite from the open end or ends of the hollow cylinder, to provide a web of a lead-containing material protruding inwardly toward the hollow cylinder on the adjacent side wall of the lock chamber, which web extends at least along a portion of the circumferential wall of the hollow cylinder and delimits a gap with it. To escape from the hollow cylinder, the X-radiation would have to penetrate the gap and be reflected multiple times in the gap, which is not the case, or is the case only to a very slight extent.

It is furthermore advantageous to provide a collar of a lead-containing material inside the lock chamber, between the hollow cylinder and the x-ray chamber; this collar surrounds a passage for the objects that is open and that leads into the x-ray chamber, and the collar advantageously extends into the vicinity of the circumferential wall of the hollow cylinder, so that practically no X-radiation can escape there from the x-ray chamber beyond the hollow cylinder to reach the inside of the lock chamber. The shielding in this region can be still further improved by mounting a protruding plate of a lead-containing material on the collar, which plate extends in the axial direction and circumferential direction along a portion of the circumferential wall of the hollow cylinder and delimits a gap with the circumferential wall. Toward the hollow cylinder, the plate expediently has a concavely curved surface, the radius of curvature of which is somewhat greater than that of the circumferential wall of the hollow cylinder. The circumferential wall, together with the plate, forms a gap in which any X-radiation penetrating it is reflected many times because of the great length of the gap and as a result is greatly attenuated.

The gap between the plate and the circumferential wall of the hollow cylinder can expediently be embodied such that the aforementioned webs of lead-containing material, protruding past the inside of the side walls or doors of the lock chamber, enter into the gap and thus increase its labyrinth effect.

Because of the horizontal rotary axis, in a further preferred embodiment the hollow cylinder can be carried by a plurality of rotatable support rollers that are in turn advantageously supported on the floor of the lock chamber. In this way, it is possible to prevent the hollow cylinder from being supported at the ceiling of the lock chamber; such support would be necessary when the rotary axis is vertical. The support rollers expediently rest against the outer surface of the circumferential wall and roll on it.

At least wherever both ends of the hollow cylinder are open, the drive of the hollow cylinder is advantageously done by means of a rotary drive that includes a belt drive. This belt drive expediently includes at least one toothed belt, which wrapped around a portion of the circumferential wall of the hollow cylinder and a drive gear wheel, located below the hollow cylinder, of a drive motor and is tensioned by means of one or more tensioning rollers.

Preferably, in operation, the hollow cylinder is rotated by approximately 180 degrees with a varying direction of rotation, in order to position the through opening alternately at the opposed sides of the lock. However, for this purpose, it is alternatively also possible to rotate the hollow cylinder with the same direction of rotation by 360 degrees.

As in the apparatus of WO 03/085416 A1, in testing wheels, the inlet-end lock chamber can be used for identifying the wheels. For that purpose, a camera is mounted above the hollow cylinder, on or near the ceiling of the lock chamber; the camera visually detects the wheel, located in the lock, from above as soon as the through opening of the hollow cylinder is pointing upward and is located between the camera and the wheel.

BRIEF DESCRIPTION OF THE DRAWINGS

The invention will be described in further detail below in terms of an exemplary embodiment shown in the drawing.

DETAILED DESCRIPTION

Figure 1:
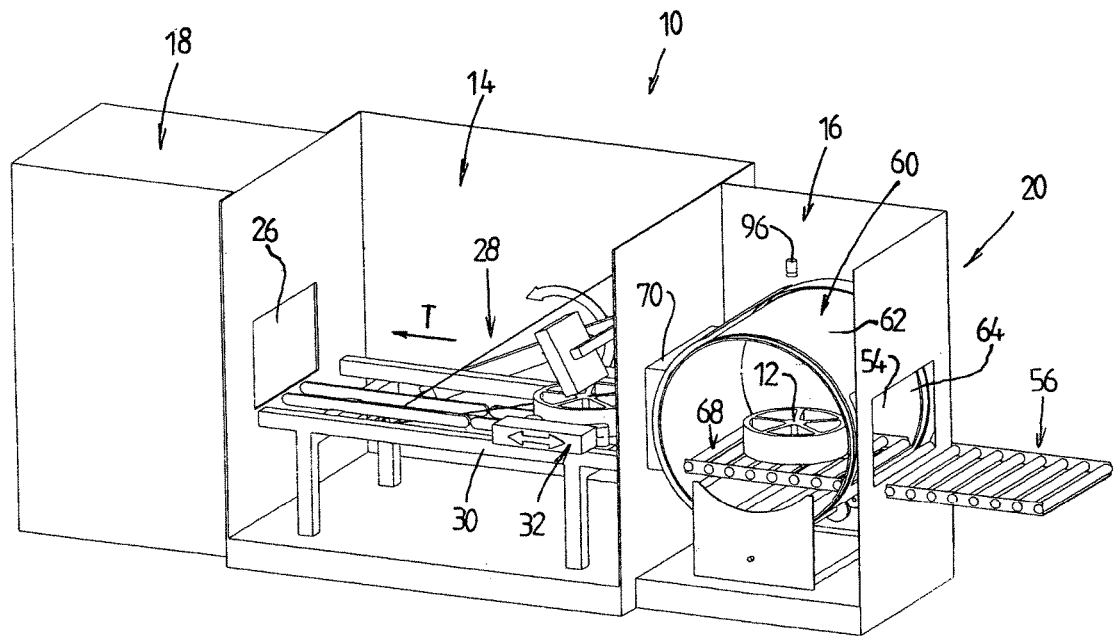
FIG. 1 shows a partly cutaway perspective view of an apparatus according to the invention for nondestructive material testing of light metal casting wheels, having a x-ray chamber and an inlet lock and an outlet lock, directly following the delivery of a wheel into the inlet lock.

The apparatus 10 shown in the drawing serves the purpose of nondestructive material testing of objects in the form of motor vehicle wheels 12 of light metal alloy with the aid of X-rays.

The apparatus 10 includes a central x-ray chamber 14, in which the material testing is performed, and two lock chambers 16, 18 of an inlet lock 20 and of an outlet lock 22, which are located on opposite sides of the x-ray chamber 14 in the transportation direction (arrow T) of the wheels 12. The apparatus 10 furthermore includes conveyor devices, with which the wheels 12 are conveyed along a rectilinear horizontal transport path, first through the inlet lock 20 into the x-ray chamber 14 and then through the outlet lock 22 out of the x-ray chamber 14. The two locks 20, 22 are meant to prevent X-radiation from escaping from the x-ray chamber 14 into the surroundings while the wheels 12 are being transported. The x-ray chamber 14 and the two locks 20, 22 have a symmetrical construction, which makes it possible to reverse the transportation direction.

The cuboid x-ray chamber 14 has four vertical walls, a floor, and a ceiling, all of which are covered with a layered layered sandwich material comprising layers of steel and lead (not shown), so that no X-radiation can escape into the surroundings through the walls, floor and ceiling. In each of the two opposed walls between the x-ray chamber 14 and the lock chambers 16, 18 of the inlet and outlet locks 20, 22, there is a rectangular passage 24, 26 for the entrance and exit of the wheels 12. The two passages 24, 26 are located opposite one another along the transport path and are not closable by means of bulkheads.

In the interior of the x-ray chamber 14, there are a fluoroscopy device 28 for fluoroscopy of the wheels 12; a manipulator 32, movable on a supporting table 30 in the transportation direction, for grasping, lifting and rotating the wheels 12; and two chain conveyors 34, 36, of which one conveys the wheels 12 from the inlet-end passage 24 to the manipulator 32, and the other conveys the wheels 12 from the manipulator 32 to the outlet-end passage 26.

The fluoroscopy device 28 includes a X-ray source 38, located below the transport path of the wheels 12, and a digital image detector 40, which is located above the transport path and the X-ray source 38.

The X-ray source 38 and the image detector 40 are mounted one above the other on a support arm 42, which is pivotable back and forth (arrow S) about a horizontal pivot axis that is perpendicular to the transportation direction. The image detector 40 is connected to the support arm 42 by a movable cantilever 44 to enable it to be moved toward and away from the X-ray source 38 along an optical axis of the radiation cone 46.

The X-ray source 38 remains continuously switched on for the duration of the material testing, even if just then there is no wheel 12 located in the radiation cone 46. As a result, X-radiation is always generated, for example including while a wheel 12 is being moved through one of the passages 24, 26. If at that time the support arm 42 is inclined by a relatively small angle, as shown in FIGS. 1 through 5, then one of each of the passages 24, 26 is located partly inside the radiation cone 46, so that direct X-radiation is aimed at this passage 24, 26.

The supporting table 30 has four vertical legs supported on the floor of the chamber 14, which are connected at their upper ends to one another by two crossbeams and two longitudinal beams. The two crossbeams form a support for the two chain conveyors 34, 36 located one behind the other, which each have two parallel conveyor chains and have a slight spacing from one another in the centre of the x-ray chamber 14. The upper runs of the conveyor chains form a horizontal supporting surface for the wheels 12.

The two longitudinal beams include linear guides for a carriage 48 of the manipulator 32, which carriage can be moved back and forth in the transporting direction by means of a drive (not shown) along the plane upper side of the longitudinal beam. The carriage 48 has four arms 50 (only partially visible), which are located in pairs opposite one another on both sides of a vertical longitudinal center plane of the x-ray chamber 14, are mounted pivotably on the carriage 48 about vertical pivot axes for adaptation to various wheel diameters, and each carry a conical roller 52 that tapers toward the top. When the arms 50 are pivoted toward one another and pressed against the rim flange of a wheel 12 for fluoroscopy, the wheel 12 is lifted upward somewhat from the inlet-end chain conveyor 34 by the conical shape of the rollers 52. At least one of the conical rollers 52 is provided with a rotary drive, in order to rotate the lifted wheel 12 about its center axis for fluoroscopy and to keep it in arbitrary rotary positions. After the fluoroscopy, the carriage 48 is moved above the outlet-end chain conveyor 36, and the arms 50 are moved apart, in order to set down the wheel 12 on the chain conveyor 36 and to convey it with that conveyor through the passage 26 into the outlet lock 22.

Figure 2:
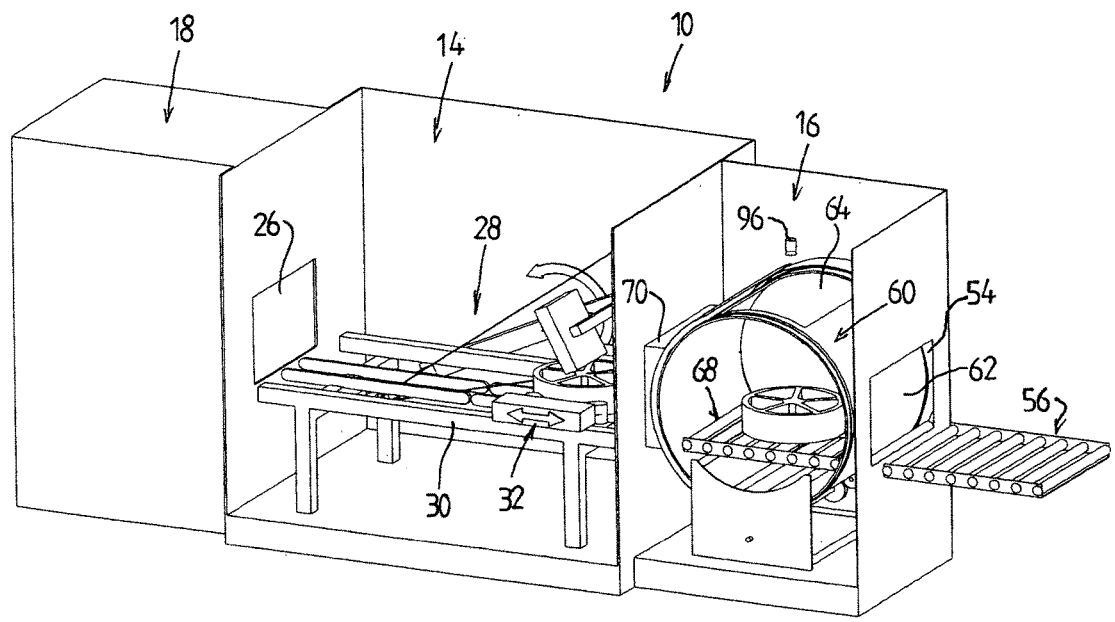
FIG. 2 shows a view corresponding to FIG. 1, but during the identification of the wheel inside the inlet lock.
Figure 3:
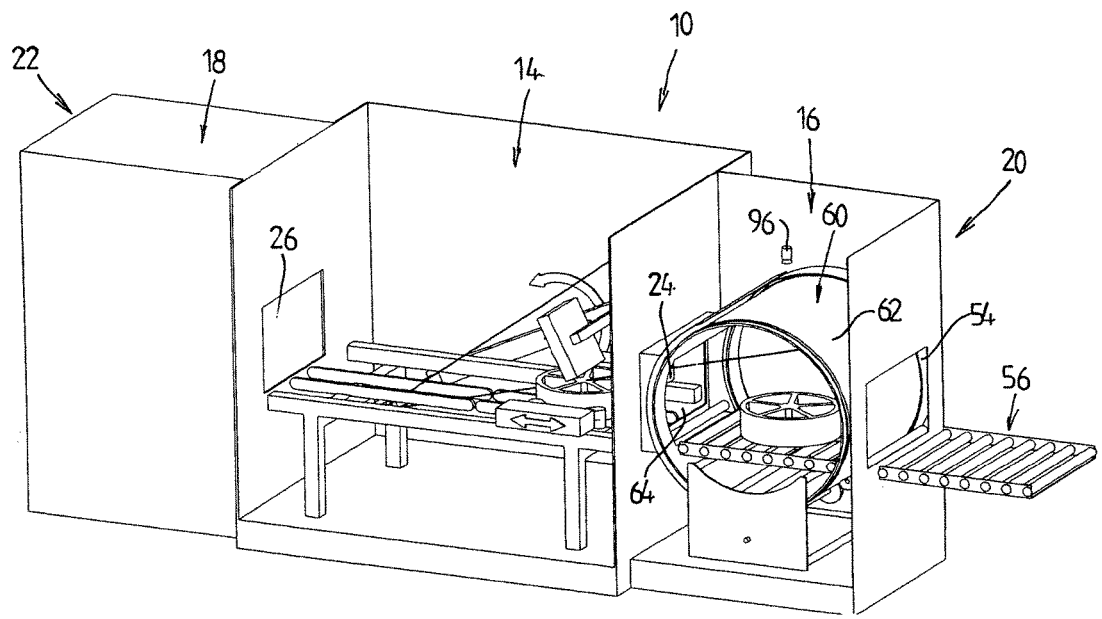
FIG. 3 shows a view corresponding to FIGS. 1 and 2, but shortly before the further transportation of the wheel into the x-ray chamber.
Figure 9:
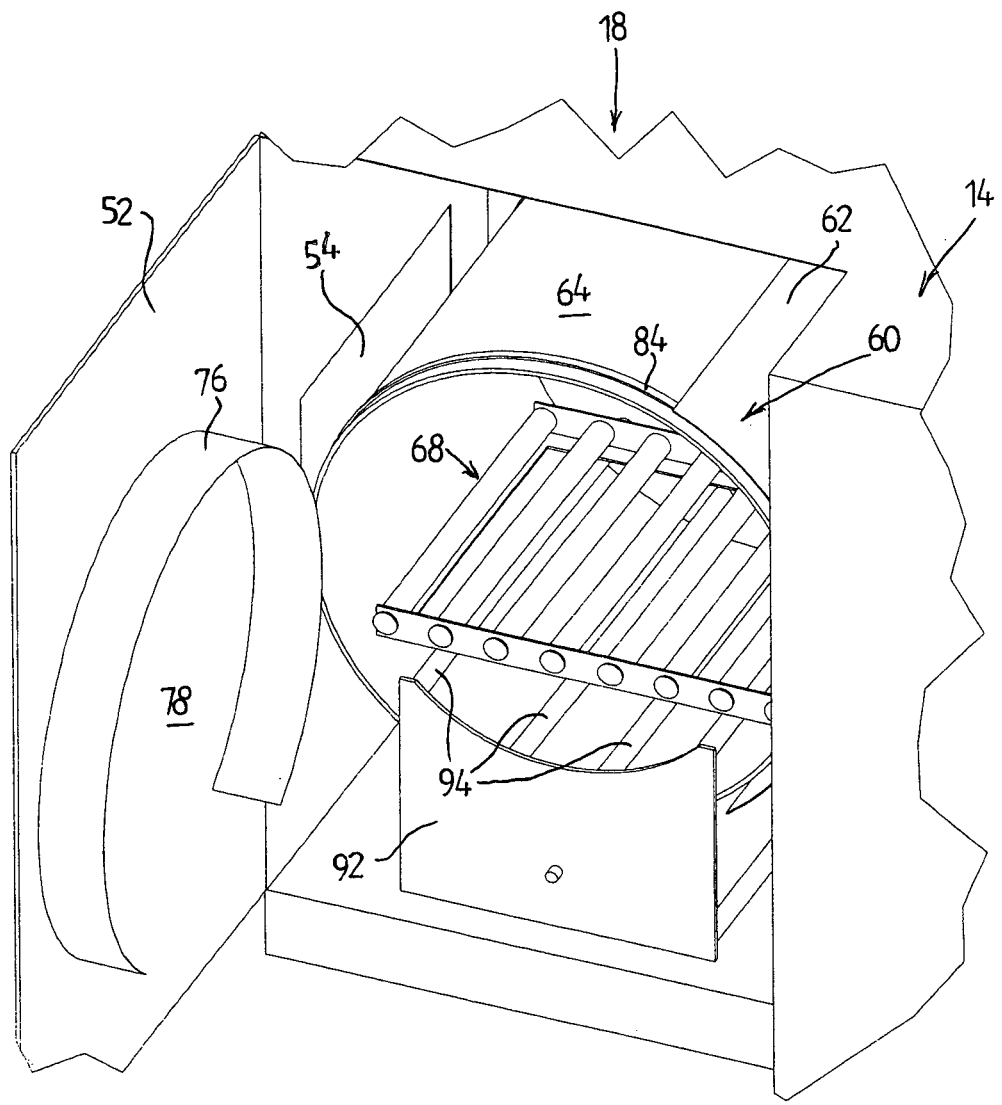
FIG. 9 shows still another enlarged partly cutaway perspective view of parts of the inlet lock.

As best shown in FIGS. 1 through 3, the two cuboid lock chambers 16, 18 are narrower than the x-ray chamber 14, in order to reduce the space needed by the apparatus 10. Each lock chamber has four vertical walls, of which at least one of the two side walls on both sides of the transporting path is embodied as a door 52, as shown in FIG. 9. The wall on the side adjacent to the x-ray chamber 14 is provided with the passage 24, 26 and is formed by the wall of the x-ray chamber 14 that is covered with the layered sandwich material comprising steel and lead layers. The opposite wall of the lock chambers 16, 16 is provided with an opening 54, serving as an inlet and outlet respectively, which is aligned with the passages 24, 26. An inlet and outlet conveyor 56 in the form of a roller conveyor with driven rollers is located upstream and downstream of these openings 54, outside the lock chamber 16, 18.

As will be described below taking the inlet lock 20 as an example, inside each lock chamber 16, 18 there is a rotatable hollow cylinder 60 that has two opposed open ends and a circumferential wall 62, which is covered with a layered sandwich material comprising steel and lead layers and in which a through opening 64 for a single wheel is made.

The hollow cylinder can, by means of a rotary drive 66 located under it, be set into rotation about a horizontal rotary axis oriented orthogonally to the transporting direction, in order to move the through opening 64 alternately in front of the inlet 54 and in front of the passage 24. Inside the hollow cylinder 60, there is a stationary roller conveyor 68 of the conveyor devices, which conveys the wheels 12 through the lock with the aid of driven conveyor rollers.

On the wall of the x-ray chamber 14 that is provided with the passage 24 or 26, inside the adjacent lock chamber 16, 18, there is one collar 70 each, which is made of a lead-containing material and surrounds the respective passage 24 and 26. As best shown in FIGS. 4, 5, 7 and 8, the collar 70, on its side oriented toward the hollow cylinder 60, has a curved, partly cylindrical plate 72, which comprises a layered sandwich material of steel and lead layers and protrudes past the collar 70 on all sides. The plate 72 has a constant radial spacing from the circumferential wall 62 of the hollow cylinder 60 and has a somewhat larger radius of curvature, so that between the plate 72 and the circumferential wall 62, a gap 74 of constant gap width is formed. The plate 72 extends in the axial direction of the hollow cylinder 60 over nearly the entire length thereof, while in the circumferential direction of the hollow cylinder 60, its projection on either side of the collar 70 is approximately equivalent to the inside width of the through opening 64 in the hollow cylinder 60.

As best shown in FIG. 9, taking the door or a door 52 of the lock chamber 18 as an example, the doors 52 are each pivotable about a vertical pivot axis for opening and closure. An annular web 76, open at the bottom and comprising the layered sandwich material of steel and lead layers, protrudes past the inside of each door 52; when the door 52 is closed, the web surrounds the adjacent open end of the hollow cylinder 60 along the mayor part of its circumference, in particular on its top and sides, and on the side toward the collar 70 protrudes into the gap 74 between the curved plate 72 and the circumferential wall 62 of the hollow cylinder 60. As a result, a kind of labyrinth is generated along the web 76 that prevents practically any escape of X-radiation from the hollow cylinder 60.

Opposite the open ends of the hollow cylinder 60, the doors 52 are likewise covered at 78 on their insides with the layered sandwich material comprising steel and lead layers, which material extends somewhat outward in the radial direction of the hollow cylinder 60 past its outer circumference or up to the web 76, so that no X-radiation can escape there from the interior of the hollow cylinder 60 through the wall or door 52 into the surroundings.

Aside from the collar 70, the plate 72, the web 76, and the layered sandwich material at 78 on the insides of the doors 52, however, the other walls, the floor and the ceiling of the lock chambers 16, 18 are not provided with a shield of lead-containing material, or are provided with an only relatively thin such shield, since because of the provisions described above practically no X-radiation can escape from the hollow cylinder 60 or past the hollow cylinder 60 into the lock chamber 16, 18.

For rotatably carrying the hollow cylinder 60, the hollow cylinder is supported on four support rollers 80, which are located in pairs in the vicinity of the two ends of the hollow cylinder 60. The rotary drive 66 of the hollow cylinder 60 includes a belt drive with two toothed belts 84, which extend at the ends of the hollow cylinder 60 around the major part of the outer circumference thereof next to the lateral edges of the curved plate 72 and are guided below the hollow cylinder 60 through a fixed deflection roller 85, a movable tension roller 86, and a drive gear wheel 88 on a shaft that is driven via a gear mechanism 82 by an electric drive motor 90. The ends of the shaft are rotatably supported in two opposed side cheeks 92, which on their insides (not visible) are provided with guides for the tension rollers 83, rotary bearings for the deflection rollers 82, and adjustable-height support elements for the support rollers 80.

The two side cheeks 92 protrude upward from the floor of the lock chamber beyond the ends of the hollow cylinder 60, and they extend upward at a slight distance from the insides of the doors 52 through gaps on the underside of the webs 76. The side cheeks 92 are connected to one another, below their concavely curved upper edge, by a plurality of cross struts 94, which together with the side cheeks 92, carry the roller conveyor 68 along with its drive (not shown), so that the roller conveyor 68, like the hollow cylinder 60, is supported on the floor of the lock chamber 16, 18 through the side cheeks 92.

Figure 4:
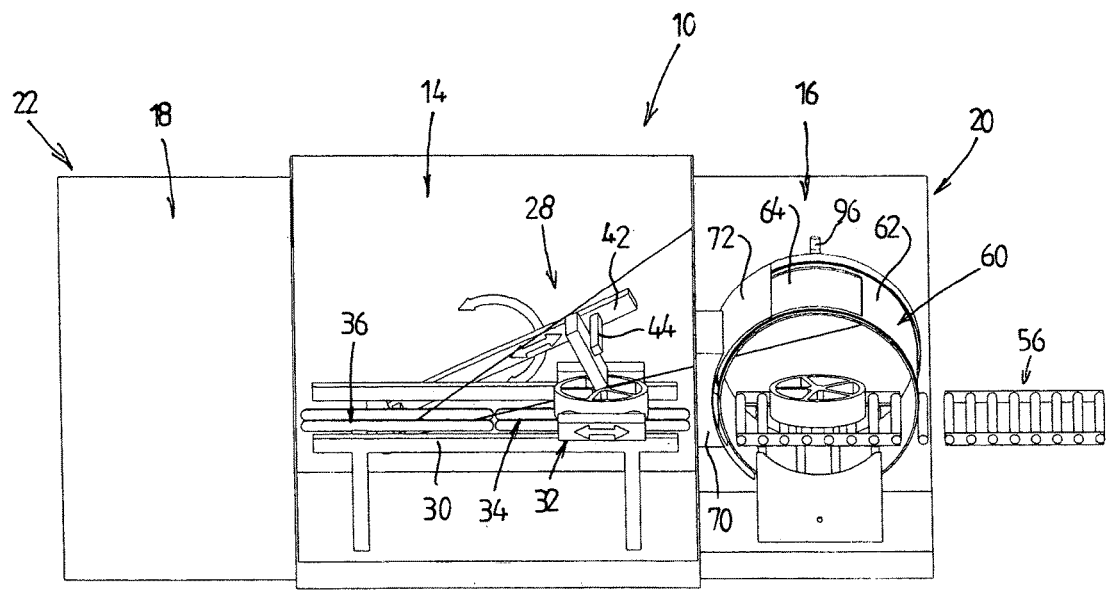
FIG. 4 shows another partly cutaway perspective view of the apparatus during the identification of the wheel in the inlet lock.
Figure 5:
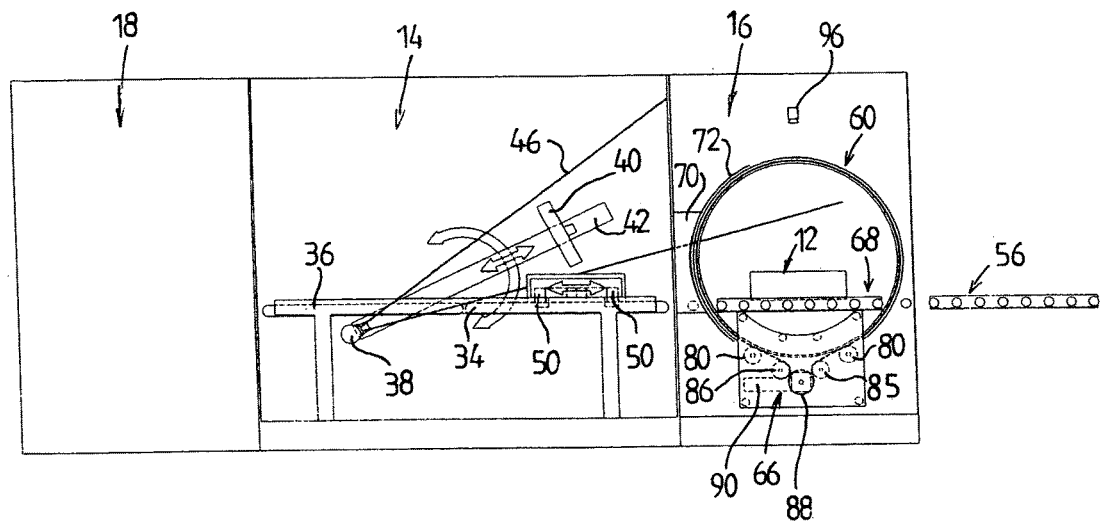
FIG. 5 shows a partly cutaway side view of the apparatus.
Figure 6:
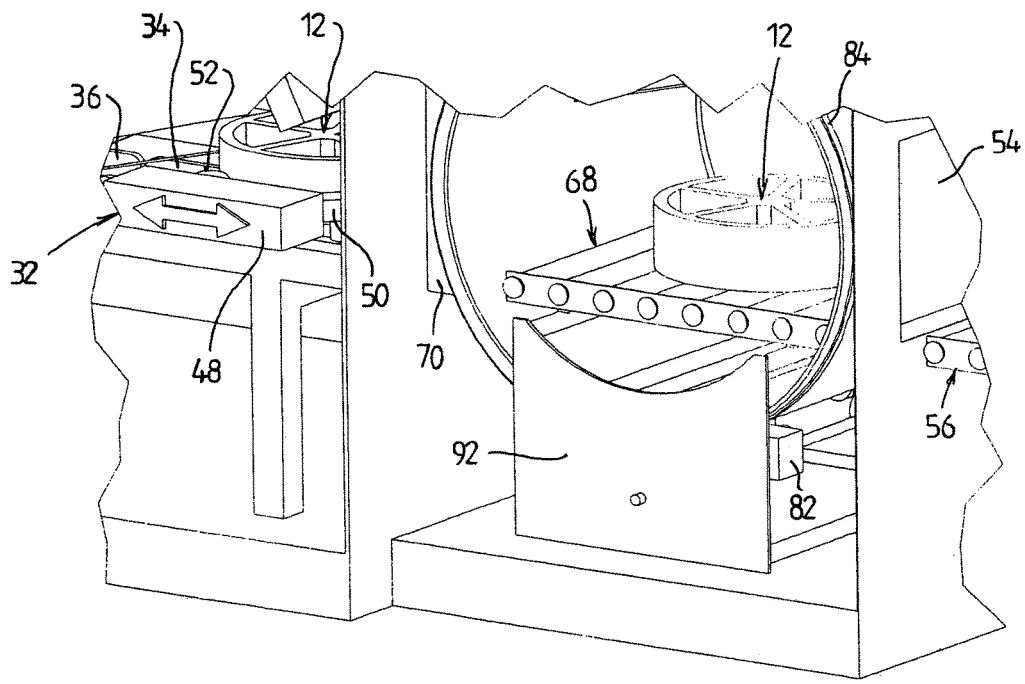
FIG. 6 shows an enlarged partly cutaway perspective view of parts of the inlet lock.
Figure 7:
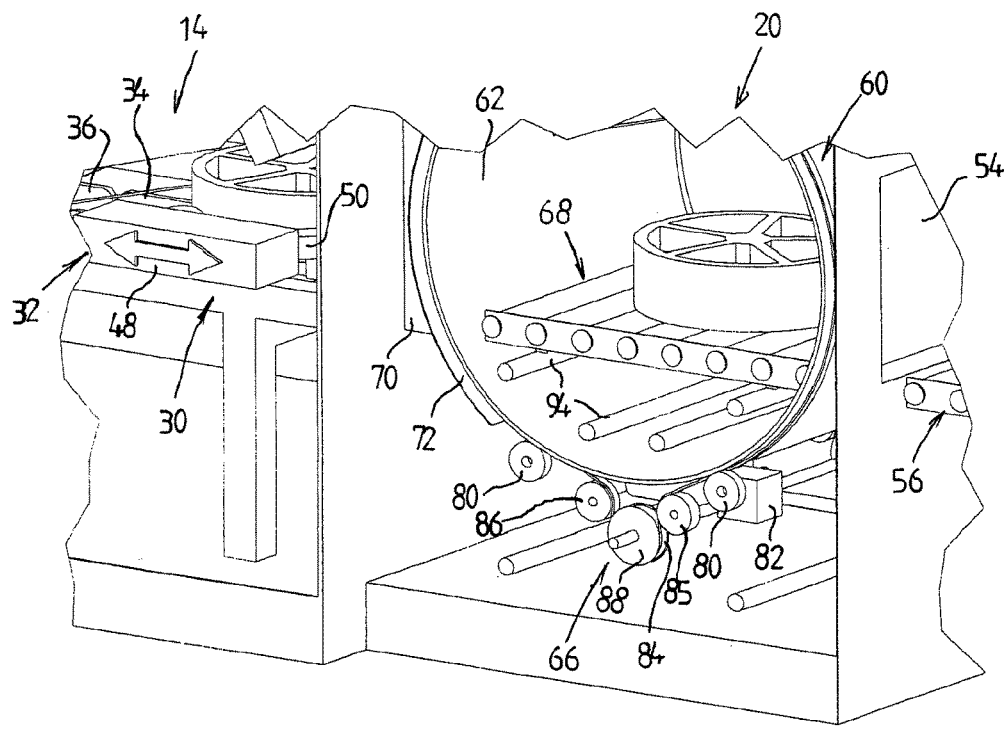
FIG. 7 shows a further partly cutaway, enlarged perspective view of parts of the inlet lock.
Figure 8:
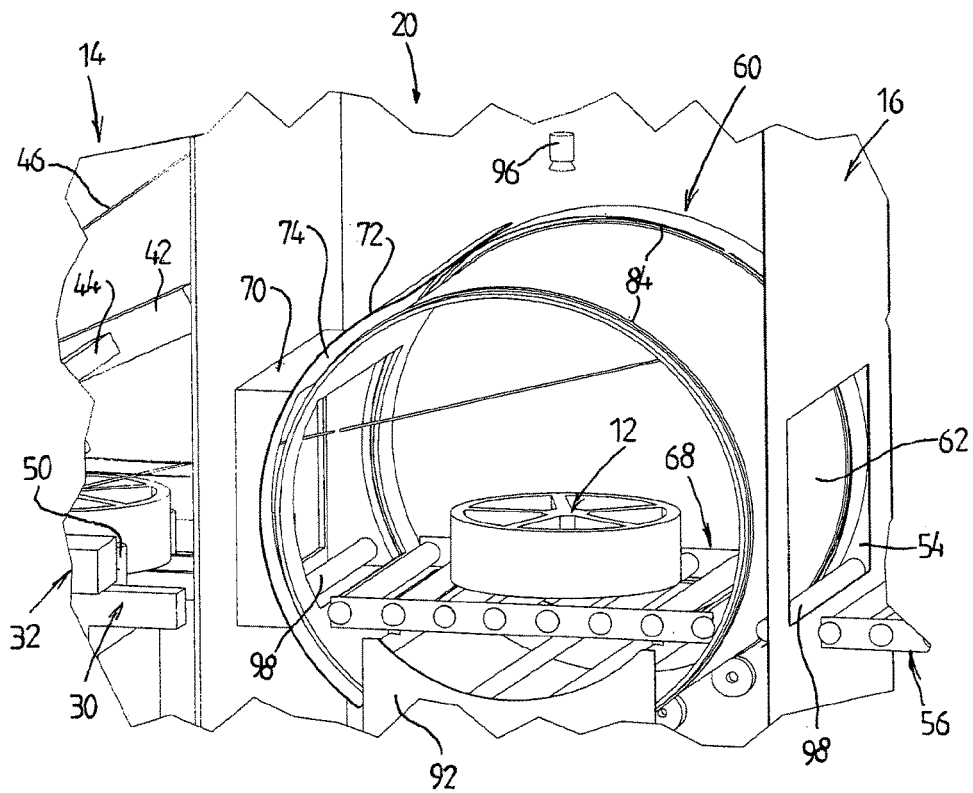
FIG. 8 shows another partly cutaway enlarged perspective view of parts of the inlet lock.

In the lock chamber 16 of the inlet lock 20, a camera 96 is mounted above the hollow cylinder 60. With the camera 96, the wheels 12 located on the roller conveyor 68 of the inlet lock 20 are detected if the through opening 64 in the circumferential wall 62 of the hollow cylinder 60 is pointing upward, as shown in FIGS. 2 and 4. The detection serves to determine or control the size and type and possible further parameters of the wheels 12, in order to use that information in the ensuing fluoroscopy in the x-ray chamber 14 for controlling the fluoroscopy device 28 and the manipulator 32.

The roller conveyors 68 are located entirely in the interior of the hollow cylinders 60 below the rotary axes thereof, and their opposite ends each have a slight distance from their circumferential walls 62. As a result, each hollow cylinder 60 is rotatable about the associated conveyor 68, and its circumferential wall 60 can move past the two opposed ends of the conveyor 68 in order to move the through opening 64 alternately in front of one of the two ends.

Furthermore, the conveyor devices inside the lock chambers 16, 18 also have two additional conveyor rollers 98. The two conveyor rollers 98 are located at the same height as the conveyor rollers of the roller conveyor 68, outside the hollow cylinder 60 between its circumferential wall 62 and the walls of the lock chamber 16, 18 that are provided with the passage 24, 26 or the inlet 56 or outlet, respectively, and can optionally be driven.

All the conveyors 34, 36, 56, 68, with their top sides, form a horizontal supporting surface for the wheels 12, as a result of which the defined rectilinear horizontal transportation path of the wheels 12 inside the apparatus 10 is provided.

What is claimed is:

1. An apparatus for nondestructive material testing of objects made of light metal casting, the apparatus comprising:
 a x-ray chamber that contains a fluoroscopy device for fluoroscopy of the objects; and
 conveyor devices for conveying the objects through at least one lock into the x-ray chamber and out of the x-ray chamber,
 wherein the lock includes a hollow cylinder, whose circumferential wall has a through opening for the objects and which is rotatable about a rotary axis in order to position the through opening alternately on a side of the lock that faces away from the x-ray chamber or on a side of the lock that faces toward the x-ray chamber, and wherein the rotary axis is oriented horizontally.

2. The apparatus of claim 1, wherein the conveyor devices in the or in each lock include a conveyor entirely surrounded by the hollow cylinder and having a supporting surface for the objects that is parallel to the rotary axis.

3. The apparatus of claim 2, wherein the supporting surface of the conveyor is spaced apart from and below the rotary axis.

4. The apparatus of claim 2, wherein the conveyor has two opposed ends, which are located in a vicinity of the circumferential wall of the hollow cylinder.

5. The apparatus of claim 2, wherein the hollow cylinder has at least one open end, and wherein the conveyor is carried by supports which extend through the open end of the hollow cylinder.

6. The apparatus of claim 5, wherein the hollow cylinder has two open ends, and wherein the supports extend through both open ends of the hollow cylinder.

7. The apparatus of claim 1, wherein the circumferential wall of the hollow cylinder comprises a material that contains lead.

8. The apparatus of claim 1, wherein the lock has a lock chamber surrounding the hollow cylinder, wherein walls, a ceiling and a floor of the chamber are provided in the vicinity of an open end or ends of the hollow cylinder and around a passage to the x-ray chamber, and with a shield that contains lead.

9. The apparatus of claim 1, wherein the lock has a lock chamber surrounding the hollow cylinder, and wherein, in the vicinity of an open end or ends of the hollow cylinder, a web of a lead-containing material protrudes inward from an adjacent wall of the lock chamber and extends in the axial direction along a portion of the circumferential wall of the hollow cylinder and defines a gap with the circumferential wall.

10. The apparatus of claim 1, further comprising a collar located between the circumferential wall of the hollow cylinder and the x-ray chamber and comprising a lead-containing material, wherein the collar surrounds a passage leading to the x-ray chamber.

11. The apparatus of claim 10, further comprising a protruding plate of a lead-containing material mounted on the collar, the protruding plate having a curved surface facing toward the hollow cylinder, wherein the curved surface extends in the axial direction and in the circumferential direction along a portion of the circumferential wall of the hollow cylinder and defines a gap with the circumferential wall.

12. The apparatus of claim 1, wherein the hollow cylinder is supported with its circumferential wall on rotatable support rollers.

13. The apparatus of claim 1, further comprising a belt drive for driving the hollow cylinder.

14. The apparatus of claim 13, wherein the belt drive includes at least one toothed belt, which extends around a portion of the circumferential wall of the hollow cylinder and around a stationary drive gear wheel.

15. The apparatus of claim 1, further comprising a camera located above the hollow cylinder in the lock, wherein the camera visually detects the objects through the through opening in the circumferential wall of the hollow cylinder.

16. The apparatus of claim 1, wherein the objects are rims or wheels for vehicles.

17. The apparatus of claim 1, wherein the objects are made of aluminum.

* * * * *